US009744082B2

(12) United States Patent
Dieringer et al.

(10) Patent No.: US 9,744,082 B2
(45) Date of Patent: *Aug. 29, 2017

(54) ABSORBENT ARTICLE WITH RECESSED BODY CONFORMING STRUCTURE

(71) Applicant: Kimberly-Clark Worldwide, Inc., Neenah, WI (US)

(72) Inventors: Jessica Annette Ives Dieringer, Neenah, WI (US); Cheri Lee Paul, Neenah, WI (US)

(73) Assignee: Kimberly-Clark Worldwide, Inc, Neenah, WI (US)

( * ) Notice: Subject to any disclaimer, the term of this patent is extended or adjusted under 35 U.S.C. 154(b) by 391 days.

This patent is subject to a terminal disclaimer.

(21) Appl. No.: 14/529,367

(22) Filed: Oct. 31, 2014

(65) Prior Publication Data

US 2015/0057631 A1 Feb. 26, 2015

Related U.S. Application Data

(62) Division of application No. 13/412,103, filed on Mar. 5, 2012, now Pat. No. 8,915,898.

(51) Int. Cl.
*A61F 13/15* (2006.01)
*A61F 13/511* (2006.01)
(Continued)

(52) U.S. Cl.
CPC .. *A61F 13/51108* (2013.01); *A61F 13/00063* (2013.01); *A61F 13/47* (2013.01);
(Continued)

(58) Field of Classification Search
CPC ................ A61F 13/00063; A61F 13/47; A61F 13/47218; A61F 13/51108; A61F 13/5323;
(Continued)

(56) References Cited

U.S. PATENT DOCUMENTS 4,475,913 A   10/1984   Hlaban
4,758,240 A    7/1988   Glassman
(Continued)

FOREIGN PATENT DOCUMENTS

EP   0 119 919 A1   9/1984
EP   0 223 487 A2   5/1987
(Continued)

OTHER PUBLICATIONS

Co-pending U.S. Appl. No. 29/414,851, filed Mar. 3, 2012, by Dieringer et al. For "Feminine Pad With Recessed Structure."
(Continued)

*Primary Examiner* — Bradley Philips
(74) *Attorney, Agent, or Firm* — Kimberly-Clark Worldwide, Inc.

(57) ABSTRACT

An absorbent article includes a body side liner, a back sheet, an absorbent body positioned between the body side liner and the back sheet, and a distribution layer positioned between the absorbent body and the back sheet. The absorbent body defines a first opening having an opening length that is at least 50% the absorbent body length. The first opening has a median anterior portion width that is greater than a median central portion width that is greater than a median posterior portion width. The first opening includes a well, a channel, and a taper. The well transitions into the channel via a first convex transition and a concave transition. The channel transitions into the taper via a second convex transition.

4 Claims, 9 Drawing Sheets

(51) Int. Cl.
*A61F 13/472* (2006.01)
*A61F 13/00* (2006.01)
*A61F 13/532* (2006.01)
*A61F 13/53* (2006.01)
*A61F 13/49* (2006.01)
*A61F 13/537* (2006.01)
*A61F 13/47* (2006.01)
*A61F 13/535* (2006.01)
*A61F 13/51* (2006.01)
*A61F 13/45* (2006.01)

(52) U.S. Cl.
CPC ...... *A61F 13/47218* (2013.01); *A61F 13/537* (2013.01); *A61F 13/5323* (2013.01); *A61F 13/4704* (2013.01); *A61F 13/49001* (2013.01); A61F 2013/1578 (2013.01); A61F 2013/4587 (2013.01); A61F 2013/51023 (2013.01); A61F 2013/51186 (2013.01); A61F 2013/5355 (2013.01); A61F 2013/530437 (2013.01); A61F 2013/530445 (2013.01); A61F 2013/53778 (2013.01); A61F 2013/53782 (2013.01)

(58) Field of Classification Search
CPC ............ A61F 13/537; A61F 2013/1578; A61F 2013/4587; A61F 2013/51023; A61F 2013/51186; A61F 2013/530437; A61F 2013/530445; A61F 13/4704; A61F 13/49001; A61F 13/53778; A61F 13/53782
See application file for complete search history.

(56) References Cited

U.S. PATENT DOCUMENTS

| | | |
|---|---|---|
| D320,274 S | 9/1991 | Douglas |
| 5,057,096 A | 10/1991 | Faglione |
| 5,219,341 A | 6/1993 | Serbiak et al. |
| 5,462,541 A | 10/1995 | Bruemmer et al. |
| 5,484,430 A | 1/1996 | Osborn, III |
| 5,545,156 A | 8/1996 | Dipalma et al. |
| 5,562,680 A | 10/1996 | Hasson |
| 5,591,148 A | 1/1997 | McFall et al. |
| 5,702,380 A | 12/1997 | Walker |
| 5,743,896 A | 4/1998 | Parker |
| 5,810,798 A | 9/1998 | Finch et al. |
| 6,160,197 A | 12/2000 | Lassen et al. |
| 6,168,583 B1 | 1/2001 | Tanji et al. |
| 6,221,460 B1 | 4/2001 | Weber et al. |
| D469,868 S | 2/2003 | Bruce et al. |
| 6,562,192 B1 | 5/2003 | Hamilton et al. |
| D483,485 S | 12/2003 | Phillips-Nicholas |
| 6,660,903 B1 | 12/2003 | Chen et al. |
| 6,667,424 B1 | 12/2003 | Hamilton et al. |
| 6,700,035 B2 | 3/2004 | Yoshimasa |
| 6,929,629 B2 | 8/2005 | Drevik et al. |
| 6,965,058 B1 | 11/2005 | Raidel et al. |
| 6,984,225 B2 | 1/2006 | Raidel et al. |
| 7,156,832 B2 | 1/2007 | Drevik et al. |
| 7,160,280 B2 | 1/2007 | Bailey |
| D571,004 S | 6/2008 | Cardin et al. |
| 7,429,689 B2 | 9/2008 | Chen et al. |
| D614,765 S | 4/2010 | Webster |
| 7,754,940 B2 | 7/2010 | Brisebois et al. |
| D630,730 S | 1/2011 | Clark |
| 7,922,706 B2 | 4/2011 | Konawa |
| D646,781 S | 10/2011 | Forbes et al. |
| D673,672 S | 1/2013 | Dieringer et al. |
| D677,787 S | 3/2013 | Dieringer et al. |
| 8,439,885 B2 | 5/2013 | Sakano et al. |
| 8,915,899 B2 | 12/2014 | Dieringer et al. |
| 2003/0120242 A1 | 6/2003 | Carlos et al. |
| 2003/0153232 A1 | 8/2003 | Raidel et al. |
| 2003/0225385 A1 | 12/2003 | Glaug et al. |
| 2005/0010185 A1 | 1/2005 | Mizutani et al. |
| 2005/0059942 A1 | 3/2005 | Krautkramer et al. |
| 2006/0229580 A1 | 10/2006 | Raidel et al. |
| 2006/0276766 A1 | 12/2006 | Kentolall |
| 2007/0135787 A1 | 6/2007 | Raidel et al. |
| 2008/0110782 A1* | 5/2008 | Burgdorf .............. A61F 13/551 206/438 |
| 2009/0204095 A1 | 8/2009 | McDaniel |
| 2010/0057031 A1 | 3/2010 | Kuroda et al. |
| 2010/0312216 A1* | 12/2010 | Periman .............. A61F 13/4755 604/385.04 |
| 2012/0037327 A1 | 2/2012 | Alkmin et al. |
| 2012/0040039 A1 | 2/2012 | Alkmin et al. |
| 2012/0041405 A1 | 2/2012 | Alkmin et al. |

FOREIGN PATENT DOCUMENTS

| | | |
|---|---|---|
| JP | 2006-263205 A | 10/2006 |
| KR | 10-2010-0047666 A | 5/2010 |
| WO | WO 92/07535 A1 | 5/1992 |
| WO | WO 95/16424 A1 | 6/1995 |
| WO | WO 97/09014 A1 | 3/1997 |
| WO | WO 2008/004961 A1 | 1/2008 |

OTHER PUBLICATIONS

Co-pending U.S. Appl. No. 13/412,169, filed Mar. 3, 2012, by Dieringer et al. For "Absorbent Article with Raised Body Conforming Structure."

Co-pending U.S. Appl. No. 29/414,860, filed Mar. 3, 2012, by Dieringer et al. For "Feminine Pad with Raised Structure."

* cited by examiner

ABSORBENT ARTICLE WITH RECESSED BODY CONFORMING STRUCTURE

PRIORITY

This application is a divisional of application Ser. No. 13/412,103, entitled "Absorbent Article with Recessed Body Conforming Structure" and filed in the U.S. Patent and Trademark Office on Mar. 5, 2012. The entirety of the prior application is hereby incorporated by reference in this application.

BACKGROUND OF THE INVENTION

Absorbent articles such as sanitary napkins, panty liners, and incontinence pads are designed to absorb and retain fluid discharges from the human body. It is desirable that such absorbent articles conform to the body of the wearer during use. An absorbent article with body-conforming structure can increase the effectiveness of the absorbent article by reducing the possibility that fluids such as menses or urine will leak past the perimeter of the absorbent article. Additionally, an absorbent article with body-conforming structure can also be more comfortable to wear as compared to similar absorbent articles without the body-conforming structure.

Maintaining an absorbent article, such as an incontinence pad, in the proper position relative to the body of the wearer is difficult because of the external forces that are exerted upon the absorbent article under dynamic conditions. These external forces may be a result of the attachment of the absorbent garment to the wearer's clothes or may be a result of body movement, in particular, thigh movement. In use, these forces may cause the absorbent article to pull away from the body or shift from the desired position.

Previous absorbent articles have attempted to introduce deformation regions or points in the article to localize the deformation and help conform the article to the body. While these attempts have had some success, there remains a need for fluid-absorbing absorbent articles with a structure adapted to intake fluid quickly, maintain a dry surface, distribute fluid effectively throughout the product, and conform to body contours during use.

SUMMARY OF THE INVENTION

In one aspect, the present invention provides an absorbent article having a body side liner, a back sheet, an absorbent body positioned between the body side liner and the back sheet, and a distribution layer positioned between the absorbent body and the back sheet. The absorbent body defines an absorbent body length and a first opening. The first opening has an opening length that is at least 50% the absorbent body length. The first opening defines an anterior portion having a median anterior portion width, a posterior portion having a median posterior portion width, and a central portion positioned between the anterior portion and the posterior portion and having a median central portion width. The median anterior portion width is greater than the median central portion width. The median central portion width is greater than the median posterior portion width. The anterior portion includes a well, the central portion includes a channel, and the posterior portion includes a taper. The well transitions into the channel via a first convex transition and a concave transition. The channel transitions into the taper via a second convex transition.

In various embodiments the first opening defines a first opening area. The absorbent body has an absorbent body perimeter that defines an absorbent body area and a minimum width. In some embodiments, the first opening area is at least 30% of the absorbent body area and the median central portion width is 25-50% the minimum width.

In some embodiments, the absorbent body includes a body side absorbent layer and an absorbent pledget layer positioned between the body side absorbent layer and the distribution layer. In some embodiments, the absorbent pledget defines an absorbent pledget length and a second opening. The second opening has a second opening length that is at least 50% the absorbent pledget length.

In some embodiments, the second opening defines a second opening area equal to the first opening area. In some embodiments, the second opening defines a second opening area less than the first opening area.

In some embodiments, the first opening defines a first opening shape and the second opening defines a second opening shape that is substantially the same as the first opening shape.

In some embodiments, the first opening defines a first longitudinal centerline and a first lateral centerline wherein the first opening is symmetric about the first longitudinal centerline and asymmetric about the first lateral centerline. Additionally, the first lateral centerline divides the first opening into an anterior half having an anterior half area and a posterior half having a posterior half area wherein the anterior half area is greater than the posterior half area.

In some embodiments, the body side absorbent layer includes concave lateral side edges that define a minimum width and the median central portion width is 25-50% the minimum width.

In another aspect, the present invention provides an absorbent article having a body side liner, a back sheet, and a body side absorbent layer positioned between the body side liner and the back sheet. The body side absorbent layer includes concave lateral side edges and a first opening and defines a body side absorbent length. The absorbent article also includes an absorbent pledget positioned between the body side absorbent layer and the back sheet. The absorbent pledget includes a second opening and defines an absorbent pledget length. The first opening has a first opening length that is at least 50% the body side absorbent layer length. The first opening defines an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width. In the first opening, the anterior portion includes a well, the central portion includes a channel, and the posterior portion includes a taper. The well transitions into the channel via a first convex transition and a concave transition. The channel transitions into the taper via a second convex transition.

The second opening has a second opening length that is at least 50% the absorbent pledget length. The second opening defines an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width. In the second opening, the anterior portion includes a well, the central portion includes a channel, and the posterior portion includes a taper. The well transitions into the channel via a first convex transition and a concave transition. The channel transitions into the taper via a second convex transition.

In various embodiments, the first opening and the second opening are symmetric about a longitudinal centerline and asymmetric about a lateral centerline. Additionally, the concave lateral edges of the body side absorbent layer define a minimum width and the minimum width is positioned between the lateral centerline and the anterior portion of the first opening.

In some embodiments, the first opening defines a first opening area and the second opening defines a second opening area less than the first opening area. Additionally, the first opening defines a first opening shape and the second opening defines a second opening shape that is substantially the same as the first opening shape.

In some embodiments, the body side absorbent comprises 30-50% superabsorbent and the absorbent pledget comprises 50-70% superabsorbent. In some embodiments, the absorbent article further includes an intake/distribution layer positioned between the absorbent pledget and the back sheet.

In some embodiments, the body side liner includes a third opening having a third opening area and a third opening shape. The third opening shape is substantially the same as the first opening shape and the second opening shape. The third opening area is less than the first opening area and less than the second opening area. In some embodiments, the third opening defines a third peripheral edge bonded directly to the intake/distribution layer to form an inner peripheral sealed edge.

In another aspect, the present invention provides an array of absorbent articles. The array includes a first absorbent article and a second absorbent article. The first absorbent article includes a first body side liner, a first back sheet, and a first absorbent body positioned between the first body side liner and the first back sheet. The first absorbent body includes a first opening and defines a first absorbent body length. The first opening has a first opening length that is at least 50% the first absorbent body length. The first opening defines a first opening area, a first opening shape, an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width.

The second absorbent article includes a second body side liner, a second back sheet, a second absorbent body positioned between the second body side liner and the second back sheet. The second absorbent body includes a second opening and defines a second absorbent body length. The second opening has a second opening length that is at least 50% the second absorbent body length. The second opening defines a second opening area, a second opening shape, an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width. The first absorbent body length is at least 10% greater than the second absorbent body length and the first opening shape is substantially the same as the second opening shape.

In some embodiments, the first absorbent body includes a first absorbent body peripheral edge that defines a first absorbent body shape. Likewise, the second absorbent body includes a second absorbent body peripheral edge that defines a second absorbent body shape. The second absorbent body shape is different than the first absorbent body shape.

In some embodiments, the array may further include a third absorbent article. The third absorbent article includes a third body side liner, a third back sheet, a third absorbent body positioned between the third body side liner and the third back sheet, and a body conforming structure positioned in direct facing relation with the third body side liner. The body conforming structure is aligned with a longitudinal centerline of the absorbent article. The body conforming structure defines an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width. The body conforming structure includes a peripheral edge that defines a body conforming shape that is substantially the same as the first opening shape and the second opening shape.

In some embodiments, the third absorbent body defines a third absorbent body length and the body conforming structure defines a body conforming structure length that is at least 50% the third absorbent body length.

DETAILED DESCRIPTION OF THE DRAWINGS

The disposable absorbent articles of the present invention include an opening in liquid communication with an intake and/or distribution layer and positioned to align with the female anatomy. Specifically, the opening is shaped and positioned such that the anterior portion of the opening is generally aligned with the urethra, the central portion of the opening is generally aligned with the labia, and the posterior portion of the opening is generally aligned with the gluteal cleft.

In use, it is believed that the anterior portion of the opening allows fluid to quickly enter the intake and/or distribution layer which accepts and temporarily holds urine insults making it less likely to run-off the topsheet surface and leak. After insult, the anterior portion is believed to quickly become saturated, thus making the fluid available to move rearward into the central portion and the posterior portion. Additionally, the geometry of the opening is believed to promote conformance of the absorbent article to the body initially and during use. Specifically, the different widths, shapes, and transitions of the various portions of the opening are believed to promote selective bending, cupping, and peaking to better conform to the wearer's body.

Figure 1:
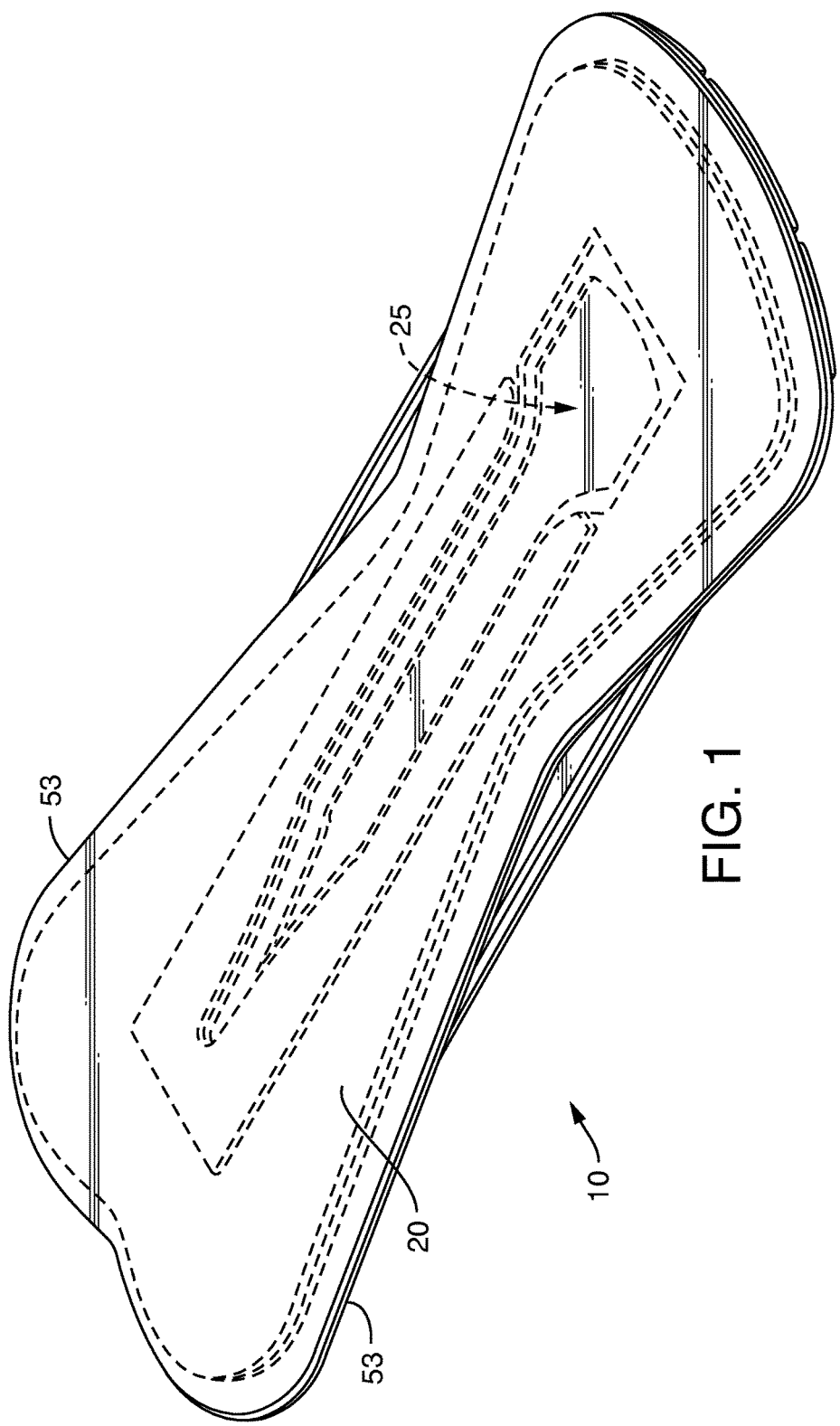
FIG. 1 representatively illustrates a top perspective view of an embodiment of the present invention.
Figure 2:
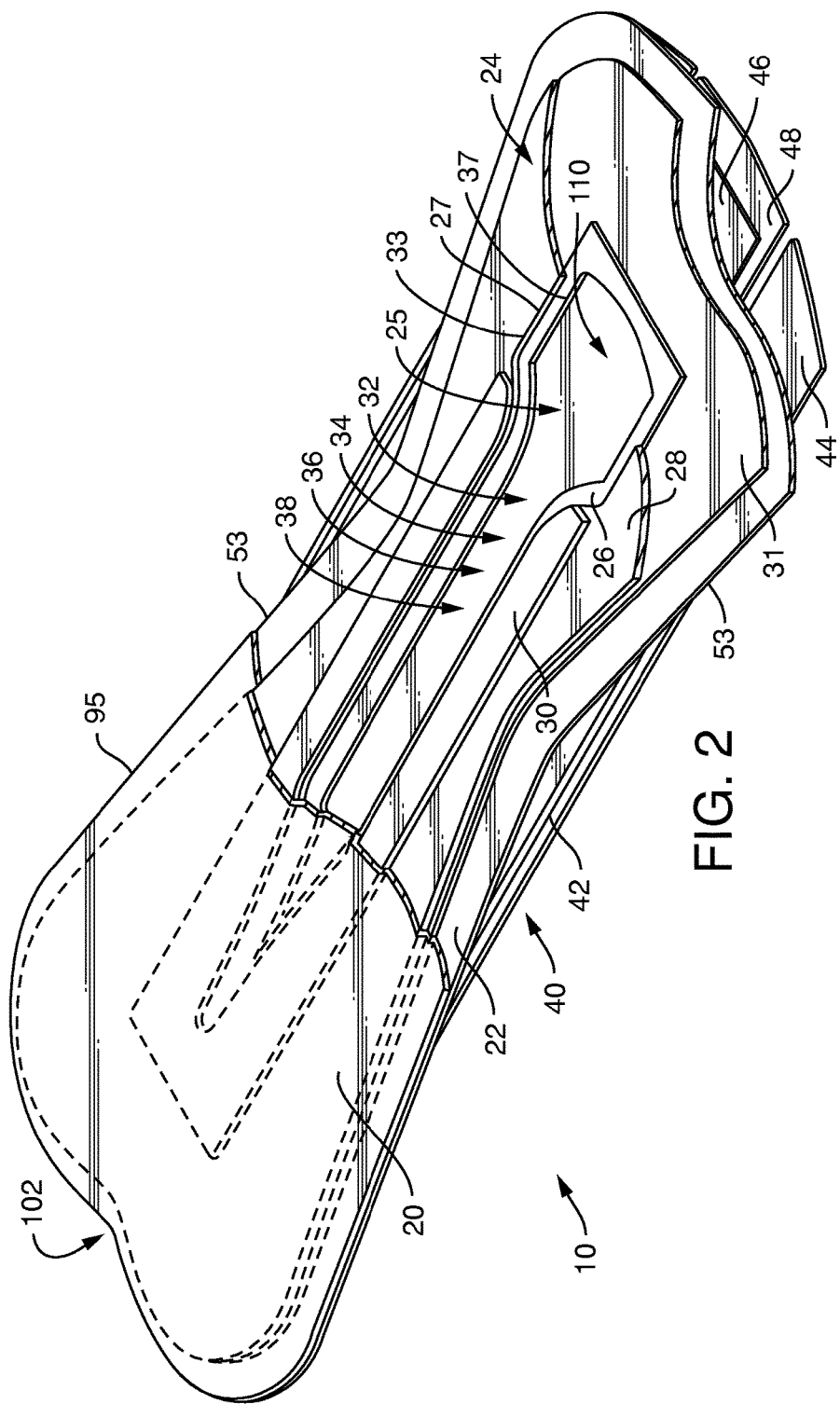
FIG. 2 representatively illustrates a top perspective view of the embodiment of FIG. 1 with portions cut away to illustrate underlying structure.
Figure 3:
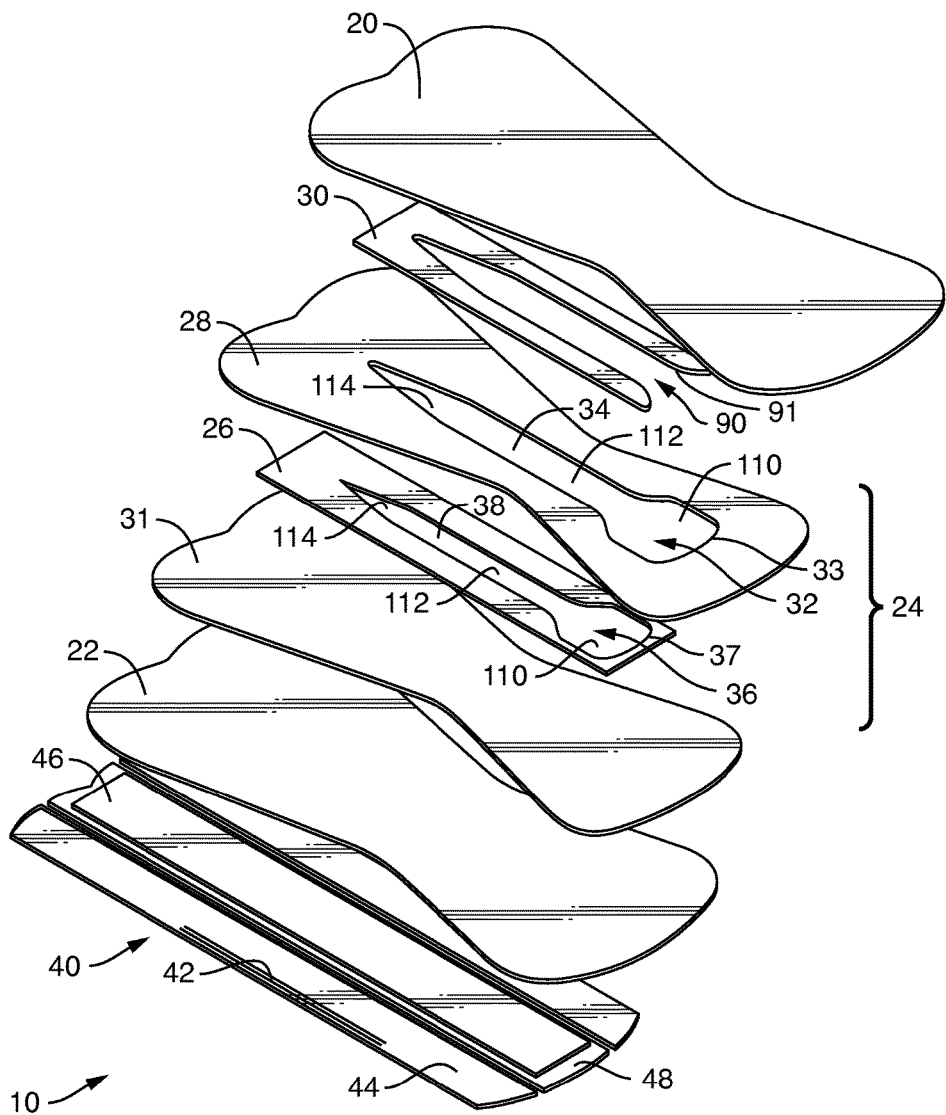
FIG. 3 representatively illustrates an expanded perspective view of the embodiment of FIG. 1.
Figure 4:
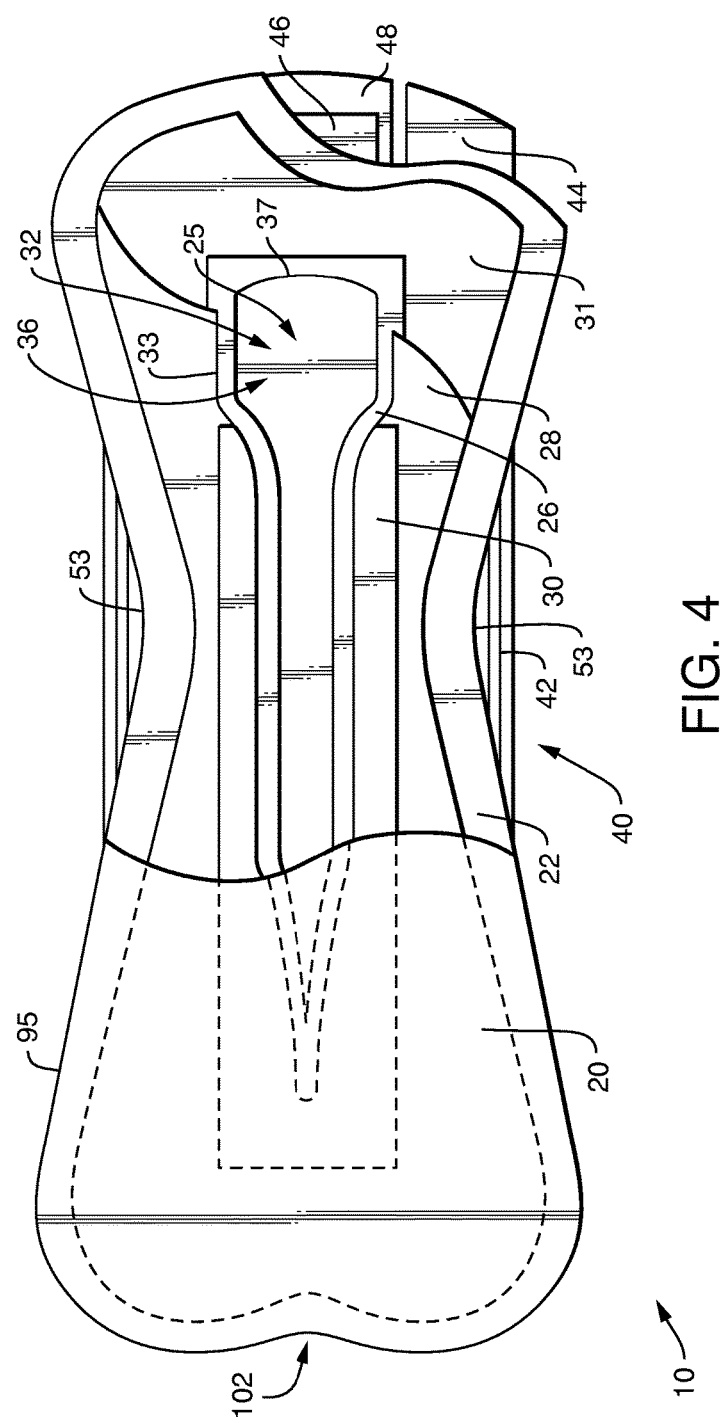
FIG. 4 representatively illustrates a top plan view of the embodiment of FIG. 1 with portions cut away to illustrate underlying structure.

FIGS. 1-4 representatively illustrate a first embodiment of a disposable absorbent article 10 of the present invention. FIG. 1 is a top perspective view of the absorbent article 10. FIG. 2 is a top perspective view of the absorbent article 10 with portions cut away to illustrate underlying structure. FIG. 3 is an expanded view of the absorbent article 10 of FIG. 1. FIG. 4 is a top plan view of the absorbent article 10 of FIG. 1 with portions cut away to reveal underlying structure. The absorbent article 10 includes a liquid-permeable top sheet (also referred to as a body side liner) 20, a substantially liquid-impermeable back sheet 22, and an absorbent body 24 positioned between the back sheet 22 and the topsheet 20. Optionally, the absorbent article 10 may also include a lower intake and/or distribution layer 31 positioned between the back sheet 22 and the absorbent body 24. Optionally, the absorbent article 10 may also include an upper intake and/or distribution layer 30 positioned between the topsheet 20 and the absorbent body 24. In some embodiments, the absorbent articles of the present invention may further include containment flaps, garment attachment adhesive, a peel strip, or combinations thereof. For example, the absorbent article 10 illustrated in FIGS. 1-4 includes containment flaps 40 which in turn include containment elastics 42 and a containment flap carrier web 44. Likewise, the absorbent article 10 of FIGS. 1-4 is shown with an optional garment attachment adhesive 46 applied to the back sheet 22 and covered with a peel strip 48.

In various embodiments, the absorbent body 24 may consist of a single layer of material or may consist of two or more layers of material. For example, the absorbent body 24 may consist of two layers of material as illustrated in FIG. 3. Specifically, the absorbent body 24 may include an absorbent pledget 26 and a body side absorbent layer 28. The absorbent pledget 26 may be positioned towards the back sheet 22 and the body side absorbent layer 28 may be superposed over the absorbent pledget 26 and positioned towards the topsheet 20 as illustrated. In other embodiments, the relative orientation of the absorbent pledget and the body side absorbent layer may be reversed (not illustrated). Whether a single layer or multiple layers, the absorbent body defines an absorbent body length, an absorbent body width, and an absorbent body perimeter. The absorbent body perimeter further defines an absorbent body area. In embodiments wherein the absorbent body includes two or more layers, the absorbent body length, the absorbent body width, the absorbent body perimeter, and the absorbent body area are defined by the furthest extent, in the plane defined by the longitudinal direction and the lateral direction, of any of the layers.

In various embodiments, the absorbent body may include an opening therein. In embodiments wherein the absorbent body includes multiple layers, one or more of the layers may include openings therein. For example, the body side absorbent layer may include an opening when the absorbent pledget does not (not illustrated). In other embodiments, the absorbent pledget may include an opening when the body side absorbent layer does not (not illustrated). In some embodiments both the body side absorbent layer and the absorbent pledget may include openings. For example, as illustrated in FIG. 3, the body side absorbent layer 28 may include a first opening 32 and the absorbent pledget 26 may include a second opening 36. Together, the first opening 32 and the second opening 36 may define or may partially define a composite opening 25 (FIG. 2). In various embodiments, the body side absorbent layer 28 and/or the absorbent pledget 26 may have openings that are completely bound by the defining layer through which the respective opening passes. For example, as illustrated in FIG. 3, the first opening 32 is completely bound by the body side absorbent layer 28. Likewise, the second opening 36 is completely bound by the absorbent pledget 26.

The first opening 32 defines a first peripheral edge 33 and defines a first area 34. Likewise, the second opening 36 defines a second peripheral edge 37 and defines a second area 38. In various embodiments, the first area 34 may be greater than, less than, or equal to the second area 38. In some embodiments, the second area 38 is less than the first area 34 as illustrated in FIGS. 2 and 3. In some embodiments, also as illustrated in FIG. 2, the first opening 32 and the second opening 36 are aligned and concentric so as to form a composite opening 25 with graduated side walls 27 which are believed to allow quick access of fluid to the individual absorbent body layers.

Figure 5:
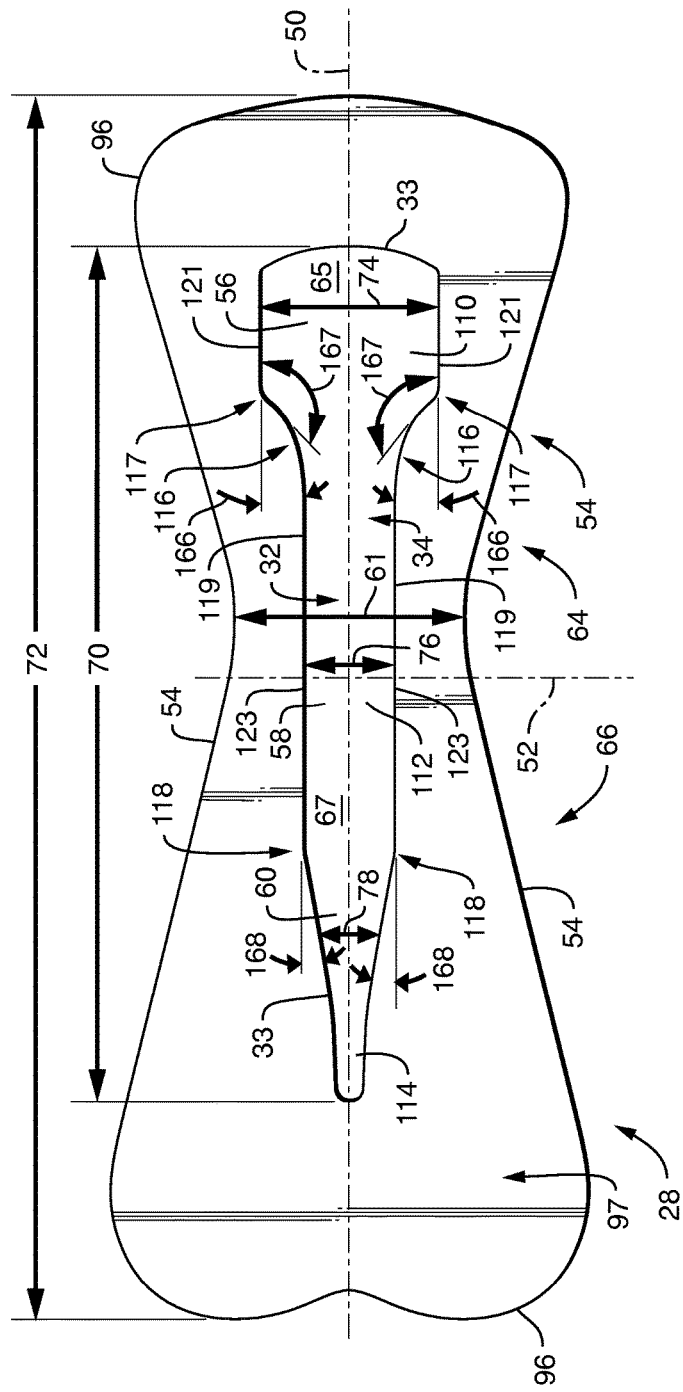
FIG. 5 representatively illustrates a top plan view of the body side absorbent layer of FIGS. 1-4.
Figure 6:
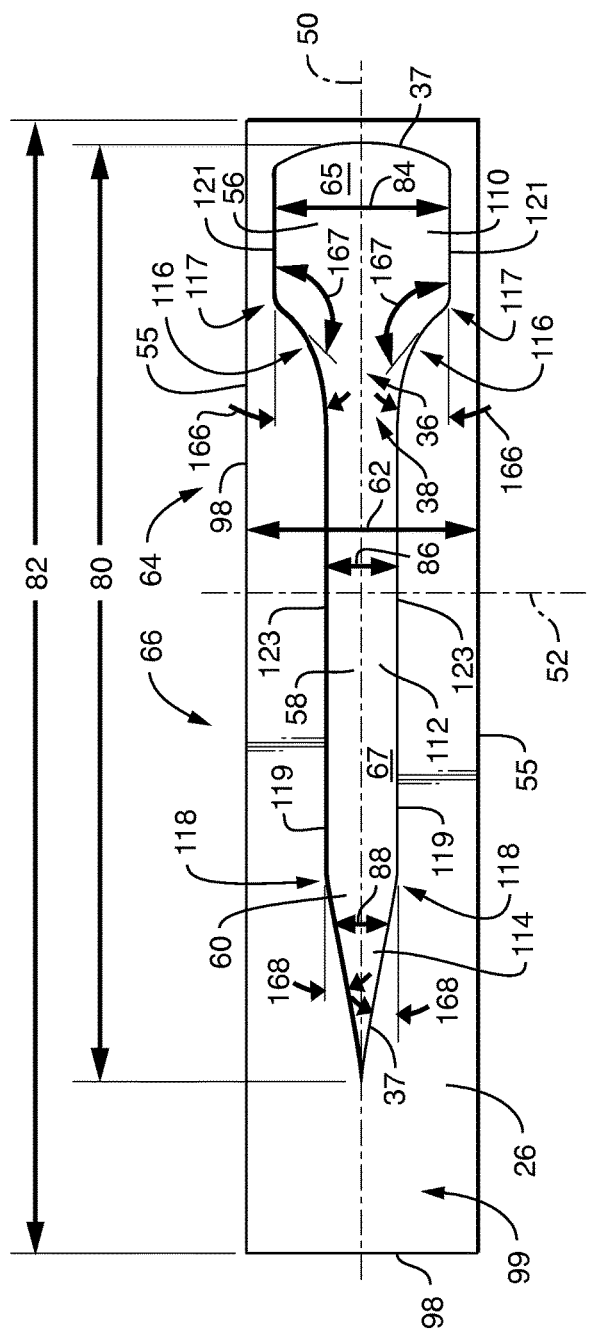
FIG. 6 representatively illustrates a top plan view of the absorbent pledget of FIGS. 1-4.

In various embodiments, the openings may have any suitable shape. In some embodiments, the openings are shaped to conform to the perineal floor of the wearer. Referring now to FIG. 5, a top plan view of the body side absorbent layer 28 of FIGS. 1-4 is representatively illustrated. The body side absorbent layer 28 includes the first opening 32 which is shaped to conform to the perineal floor of the wearer. The first opening 32 defines a first opening peripheral edge 33 and also defines a first opening area 34. Likewise, FIG. 6 representatively illustrates a top plan view of the absorbent pledget 26 of FIGS. 1-4. The absorbent pledget 26 includes the second opening 36 which is also shaped to conform to the perineal floor of the wearer. The second opening 36 defines a second opening peripheral edge 37 and also defines a second opening area 38.

In various embodiments, the first opening 32 and/or the second opening 36 may be symmetrical about a longitudinal centerline 50 of the respective opening. In some embodiments, the first opening 32 and/or the second opening 36 may be asymmetrical about a lateral centerline 52 of the respective opening. For example, as illustrated in FIGS. 5 and 6, the first opening 32 and the second opening 36 are both symmetrical about the longitudinal centerline 50 and both are asymmetrical about the lateral centerline 52.

The lateral centerline 52 divides the respective openings into an anterior half 64 and a posterior half 66. The anterior half 64 defines an anterior half area 65 and the posterior half 66 defines a posterior half area 67. As used herein, the term "anterior" refers to the portion of the opening, layer, or article that is adapted to be oriented towards the front of the wearer in normal use. Likewise, as used herein, the term "posterior" refers to the portion of the opening, layer, or article that is adapted to be oriented towards the back of the wearer in normal use. In various embodiments, the anterior half area 65 is greater than the posterior half area 67.

The various openings of the present invention also define an anterior portion 56, a posterior portion 60, and a central portion 58 positioned between the anterior portion 56 and the posterior portion 60. The anterior portion 56 is defined as the anterior third of the opening, the central portion 58 is defined as the middle third of the opening, and the posterior portion 60 is defined as the posterior third of the opening, all as measured relative to the longitudinal centerline 50.

In some embodiments, the absorbent articles of the present invention include lateral side edges of any suitable shape. For example, the lateral side edges may be straight or may have an arcuate shape such as concave, convex, wavy, or combinations thereof. Referring again to FIGS. 1 and 4, the absorbent article 10 is illustrated with lateral side edges 53 that are concave. The combination of the two lateral side edges 53 in this embodiment combine to create a curved shape. Likewise, the absorbent body of the present invention may include lateral side edges of any suitable shape. For example, the lateral side edges of the absorbent body may be straight or may have an arcuate shape, such as concave, convex, wavy, or combinations thereof. Likewise, one or more of the layers of the absorbent body may include lateral side edges that are straight, concave, convex, or combinations thereof. For example, referring now to FIG. 5, the body side absorbent layer 28 is illustrated with lateral side edges 54 that are concave. The concave lateral side edges 54 define a minimum width 61. In comparison, FIG. 6 illustrates the absorbent pledget 26 with lateral side edges 55 that are straight. The straight lateral side edges 55 define a minimum width 62.

In some embodiments, the minimum width of the body side absorbent layer is generally aligned with the lateral centerline of the first opening (not illustrated). In some embodiments, the minimum width 61 of the body side absorbent layer 28 is aligned between the lateral centerline of the first opening 32 and the anterior portion 56 of the first opening 32 as illustrated in FIG. 5.

In some embodiments, the first opening may have a shape that is different than the shape of the second opening (not illustrated). In some embodiments, the first opening 32 may have a shape that is the same or is substantially the same as the shape of the second opening 36. For example, referring now to FIGS. 5 and 6, the shape of the first opening 32 and the second opening 36 are substantially the same.

As illustrated, the anterior portion 56 of both openings 32 and 36 includes a well portion 110 that is generally rectangular in shape and has a relatively wide lateral dimension. In use, the well portion 110 is adapted to be positioned adjacent to the user's urethra. This positioning in conjunction with this shaping of the well portion 110 is believed to minimize folding of the absorbent article in this region and thereby preserve the void volume of the well portion 110 to receive body fluids.

Likewise, the central portion 58 of both openings 32 and 36 includes a channel portion 112 that is generally rectangular in shape and has a longitudinal dimension that is greater than the lateral dimension. In use, the channel portion 112 is adapted to be positioned proximate the labia. This positioning in conjunction with the shaping of the channel portion 112 is believed to allow compression of the absorbent article 10, the body side absorbent layer 28 and/or the absorbent pledget 26 by the user's legs while still allowing fluid to move freely between the anterior portion 56 and the posterior portion 60.

The posterior portion 60 of both openings 32 and 36 includes a taper portion 114 that is generally shaped like an acute triangle in which the smallest of the three angles is located at the posterior end of the shape. In various embodiments, the taper portion 114 of either or both the first opening 32 or the second opening 36 may come to a relatively sharp corner as illustrated in FIG. 6 or may come to a more rounded corner as illustrated in FIG. 5. In use, the taper portion 114 is adapted to be positioned proximate the gluteal cleft. This positioning in conjunction with the shaping of the taper portion 114 is believed to promote a longitudinal peak in the posterior portion of the absorbent article that aligns with the gluteal cleft.

The transition between the well portion and the channel portion is marked by a distinct but gentle change in curvature. In some embodiments, the longitudinal edges 119 of the well portions 110 include sections 121 that are generally parallel to the longitudinal centerline 50. Likewise, in some embodiments, the longitudinal edges 119 of the channel portions 112 include sections 123 that are generally parallel to the longitudinal centerline 50. In these and other embodiments, the well portions 110 transition into the channel portions 112 with both a first convex transition 117 and a concave transition 116 along both longitudinal edges 119 of both openings 32 and 36. The first convex transition 117 may define any suitable angle 167. In some embodiments, the angle 167 may be 110 to 160 degrees, 120 to 150 degrees, or about 135 degrees. Likewise, the concave transition 116 may define any suitable angle 166. In some embodiments, the angle 166 may be 30 to 60 degrees, 40 to 50 degrees, or about 45 degrees. It is believed that these transitions and these angles create localized deformation regions that act as stress concentrators. In use, the absorbent articles tend to create gentle bends proximate the stress concentrators and thus facilitate conformance of the article to the body at that position.

The transition between the channel portion and the taper portion is also marked by a distinct change in curvature. For example, the channel portions 112 transition into the taper portions 114 at a second convex transition 118 along both longitudinal edges 119 of both openings 32 and 36. The second convex transition 118 may define any suitable angle 168. In some embodiments, the angle 168 may be 5 to 30 degrees, 10 to 20 degrees, or about 10 degrees. These transitions are also believed to create localized deformation regions that act as stress concentrators. In use, the concave transitions 116 and the convex transitions 118 are believed to promote gentle controlled bending of the absorbent article at the location of the stress concentrators. This controlled bending further allows the absorbent article to conform to the wearer's body and allows the well portion, the channel portion, and the taper portion to be properly aligned with the user's body.

In some embodiments, the absorbent article 10 may have a perimeter 95 of any suitable shape as discussed above. For example, in some embodiments, the perimeter 95 may include a concave dip 102 in the posterior portion of the absorbent article 10 as illustrated in FIGS. 2 and 4. In some embodiments, the concave dip 102 may be substantially aligned with the longitudinal centerline of the first opening 32 and/or the second opening 36 to promote a longitudinal peak in the posterior portion of the absorbent article 10 during use.

Referring to FIG. 5, the first opening 32 has a first opening length 70. Likewise, the body side absorbent layer 28 has a body side absorbent length 72. In a first embodiment, the body side absorbent length 72 may be 160 to 190 mm, 170 to 180 mm, or about 175 mm. In these embodiments, the first opening length 70 may be 110 to 135 mm, 115 to 125 mm, or about 120 mm. In a second embodiment, the body side absorbent length 72 may be 235 to 265 mm, 245 to 255 mm, or about 250 mm. In these embodiments, the first opening length 70 may be 165 to 190 mm, 175 to 185 mm, or about 180 mm. In a third embodiment, the body side absorbent length 72 may be 275 to 305 mm, 280 to 300 mm, or about 290 mm. In these embodiments, the first opening length 70 may be 190 to 215 mm, 200 to 210 mm, or about 205 mm. In a fourth embodiment, the body side absorbent length 72 may be 325 to 410 mm, 335 to 345 mm, or about 340 mm. In these embodiments, the first opening length 70 may be 225 to 250 mm, 235 to 245 mm, or about 240 mm. In various embodiments, the first opening length 70 may be at least 50%, at least 60%, or at least 70% of the body side absorbent length 72.

The first opening 32 has a first opening width. The first opening width may be variable along the longitudinal centerline 50. For example, the first opening 32 defines a median anterior portion width 74, a median central portion width 76, and a median posterior portion width 78. As used herein, the "median width" of a given portion is the numeric value separating the higher half of the widths within a given portion from the lower half of the widths within the same portion. The median width can be determined by measuring the width of a given portion at 1 mm intervals along the longitudinal centerline, arranging the measured values from lowest to highest and selecting the middle value. If there is an even number of measurements, then the median width is the average of the middle two measurements. In some embodiments, the median anterior portion width 74 is greater than the median central portion width 76, which is greater than the median posterior portion width 78. In some embodiments, the median anterior portion width 74 may be 40-60 mm, 45-55 mm, or about 52 mm. In some embodiments, the median central portion width 76 may be 10-40 mm, 20-30 mm, or about 27 mm. In some embodiments, the median posterior portion width 78 may be 7-30 mm, 10-20 mm, or about 15 mm.

The body side absorbent layer 28 also defines a minimum width 61. In the first embodiment, the minimum width 61 may be 40 to 65 mm, 45 to 60 mm, or about 55 mm. In the second embodiment, the third embodiment, and the fourth embodiment, the minimum width 61 may be 50 to 75 mm, 55 to 65 mm, or about 60 mm. In some embodiments, the median central portion width 76 of the first opening 32 is 25-50% the minimum width 61 of the body side absorbent layer 28. In some embodiments, the median central portion width 76 of the first opening 32 is 40-45% the minimum width 61 of the body side absorbent layer 28.

The first opening 32 defines a first opening peripheral edge 33 which in turn defines a first opening area 34. Likewise, the body side absorbent layer 28 defines a body side absorbent perimeter 96 and the body side absorbent perimeter 96 defines a body side absorbent area 97. The body side absorbent area 97 includes the first opening area 34. In the first embodiment, the body side absorbent area 97 may be 90 to 110 cm$^2$, 95 to 105 cm$^2$, or about 100 cm$^2$. In these embodiments, the first opening area 34 may be 30 to 40 cm$^2$, 32 to 36 cm$^2$, or about 34 cm$^2$. In the second embodiment, the body side absorbent area 97 may be 180 to 210 cm$^2$, 190 to 200 cm$^2$, or about 195 cm$^2$. In these embodiments, the first opening area 34 may be 30 to 45 cm$^2$, 35 to 40 cm$^2$, or about 39 cm$^2$. In the third embodiment, the body side absorbent area 97 may be 220 to 260 cm$^2$, 230 to 250 cm$^2$, or about 240 cm$^2$. In these embodiments, the first opening area 34 may be 40 to 55 cm$^2$, 45 to 50 cm$^2$, or about 48 cm$^2$. In the fourth embodiment, the body side absorbent area 97 may be 300 to 390 cm$^2$, 310 to 335 cm$^2$, or about 325 cm$^2$. In these embodiments, the first opening area 34 may be 55 to 75 cm$^2$, 60 to 70 cm$^2$, or about 65 cm$^2$. In various embodiments, the first opening area 34 may be at least 15%, at least 20%, or at least 30% of the body side absorbent area 97. In some embodiments, the first opening area 34 may be about 20% of the body side absorbent area 97.

Referring now to FIG. 6, the second opening 36 has a second opening length 80. Likewise, the absorbent pledget 26 has an absorbent pledget length 82. In the first embodiment, the absorbent pledget length 82 may be 140 to 160 mm, 145 to 155 mm, or about 150 mm. In these embodiments, the second opening length 80 may be 125 to 135 mm, 128 to 132 mm, or about 130 mm. In the second embodiment, the absorbent pledget length 82 may be 165 to 185 mm, 170 to 180 mm, or about 175 mm. In these embodiments, the second opening length 80 may be 150 to 165 mm, 155 to 160 mm, or about 157 mm. In the third embodiment, the absorbent pledget length 82 may be 185 to 215 mm, 190 to 210 mm, or about 200 mm. In these embodiments, the second opening length 80 may be 170 to 190 mm, 175 to 185 mm, or about 180 mm. In the fourth embodiment, the absorbent pledget length 82 may be 240 to 270 mm, 250 to 260 mm, or about 255 mm. In these embodiments, the second opening length 80 may be 200 to 225 mm, 205 to 215 mm, or about 210 mm. In various embodiments, the second opening length 80 may be at least 50%, at least 60%, at least 70%, or at least 80% of the absorbent pledget length 82.

The second opening 36 has a second opening width. The second opening width may be variable along the longitudinal centerline 50. For example, the second opening 36 defines a median anterior portion width 84, a median central portion width 86, and a median posterior portion width 88. In some embodiments, the median anterior portion width 84 is greater than the median central portion width 86, which is greater than the median posterior portion width 88. In some embodiments, the median anterior portion width 84 may be 30-50 mm, 35-45 mm, or about 42 mm. In some embodiments, the median central portion width 86 may be 10-25 mm, 12-20 mm, or about 17 mm. In some embodiments, the median posterior portion width 88 may be 1-20 mm, 5-15 mm, or about 7 mm.

In some embodiments, the absorbent pledget 26 has a minimum width 62 of 40 to 60 mm or about 51 mm. In some embodiments, the median central portion width 76 of the second opening 36 is 25-50% the minimum width 62 of the absorbent pledget 26. In some embodiments, the median central portion width 76 of the second opening 36 is 30-40% the minimum width 62 of the absorbent pledget 26.

The second opening 36 defines a second opening peripheral edge 37 which in turn defines a second opening area 38. Likewise, the absorbent pledget 26 defines an outer perimeter 98 and the outer perimeter 98 defines an absorbent pledget area 99. The absorbent pledget area 99 includes the second opening area 38. In the first embodiment, the absorbent pledget area 99 may be 65 to 90 cm$^2$, 70 to 80 cm$^2$, or about 75 cm$^2$. In these embodiments, the second opening area 38 may be 17 to 21 cm$^2$. In the second embodiment, the absorbent pledget area 99 may be 70 to 110 cm$^2$, 75 to 100 cm$^2$, or about 89 cm$^2$. In these embodiments, the second opening area 38 may be 20 to 30 cm$^2$, 22 to 27 cm$^2$, or about 24 cm$^2$. In the third embodiment, the absorbent pledget area 99 may be 80 to 120 cm$^2$, 85 to 110 cm$^2$, or about 102 cm$^2$. In these embodiments, the second opening area 38 may be 25 to 35 cm$^2$, 27 to 32 cm$^2$, or about 29 cm$^2$. In the fourth embodiment, the absorbent pledget area 99 may be 100 to 160 cm$^2$, 120 to 140 cm$^2$, or about 130 cm$^2$. In these embodiments, the second opening area 38 may be 30 to 45 cm², 35 to 40 cm², or about 39 cm². In various embodiments, the second opening area 38 may be at least 20%, at least 25%, or at least 30% the absorbent pledget area 99. In some embodiments, the second opening area 38 may be 25-30% the absorbent pledget area 99.

In some embodiments, the absorbent article may optionally include an upper distribution and/or intake layer. For example, referring again to FIGS. 3 and 4, the absorbent article 10 is illustrated with an upper distribution/intake layer 30 positioned between the body-side absorbent layer 28 and the top sheet 20. In various embodiments, the upper distribution/intake layer may include a third opening 90 having a third opening peripheral edge 91. In various embodiments, the opening in the upper distribution/intake layer may be fully bound by the upper distribution/intake layer (not shown). In other embodiments, the third opening 90 in the upper distribution/intake layer 30 may be partially bound by the upper distribution/intake layer 30 as illustrated in FIGS. 2-4.

The upper distribution/intake layer 30 is believed to provide an additional body conforming barrier and temporary fluid storage region for fluid moving in the lateral and posterior directions. This barrier is believed to result from the deformation and conformance of this layer into and around body creases as a result of the resilience and low force required to deform this layer.

In some embodiments, the absorbent article may optionally include a lower distribution/intake layer. For example, referring again to FIGS. 2-4, absorbent article 10 is illustrated with a lower distribution/intake layer 31 positioned between the back sheet layer 22 and the absorbent body 24. In various embodiments, the lower distribution/intake layer 31 may be coextensive with the absorbent body 24 as illustrated in FIG. 2. In some embodiments, the lower distribution/intake layer may be smaller or larger than the absorbent body (not illustrated). The openings 32, 36, and/or 90 (collectively the composite opening 25) of the absorbent article are positioned such that the anterior portion 56 is adjacent to the user's urethral opening during use. When a urine insult occurs, the fluid passes through the topsheet and into the composite opening 25 and then enters the lower distribution/intake layer 31. It is believed that the urine is quickly distributed into the central and posterior portions 58 and 60 respectively and over time the fluid is distributed throughout the lower distribution/intake layer 31 and is passed into the garment side of the absorbent body 24 and/or absorbent pledget 26. This intake and distribution arrangement is believed to result in an absorbent structure with relatively dry upper layers.

An additional advantage of the present invention is that the shape of the openings allows the absorbent article to compress and expand when pressure is applied and removed by the movement of the upper thighs during wear. This product feature is believed to provide improved dynamic fit.

Figure 7:
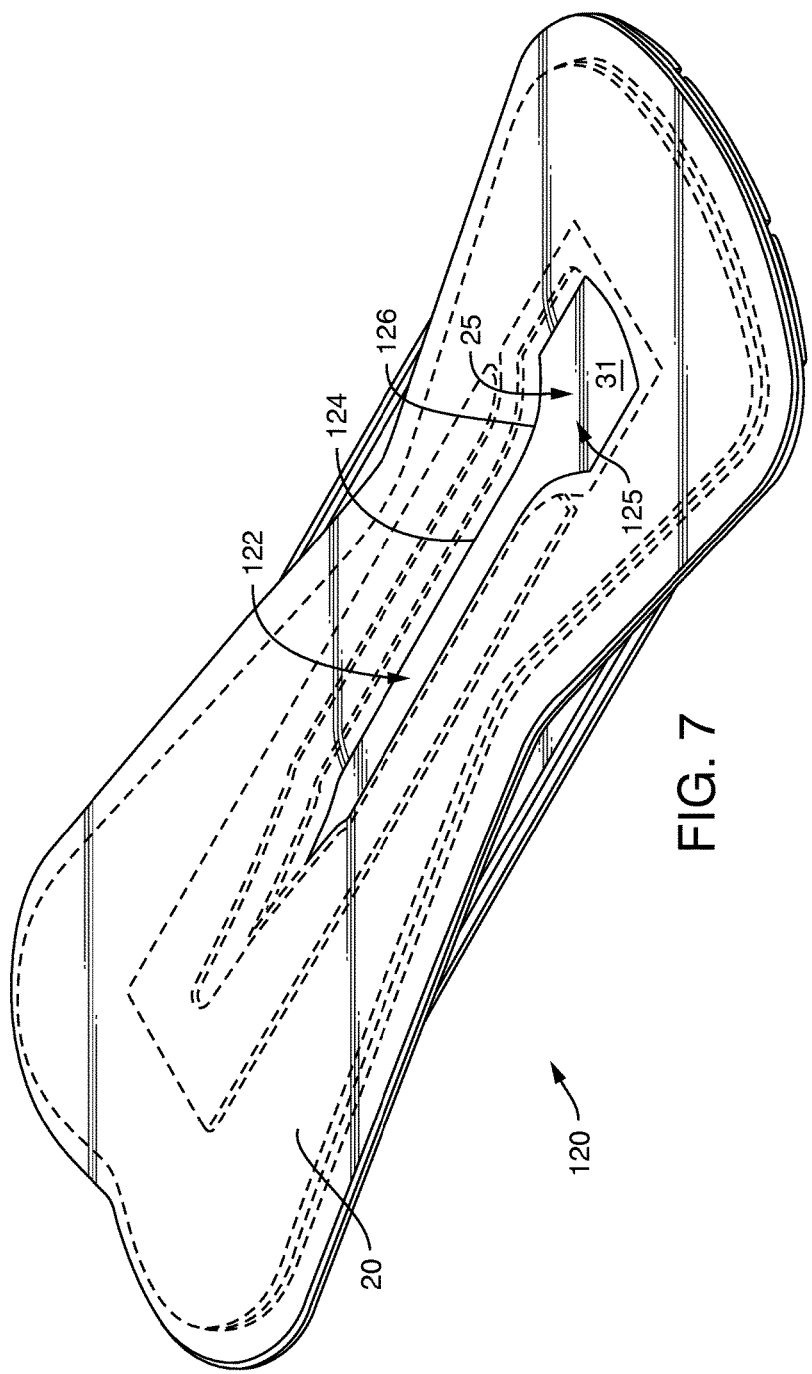
FIG. 7 representatively illustrates a top perspective view of another embodiment of the present invention.
Figure 8:
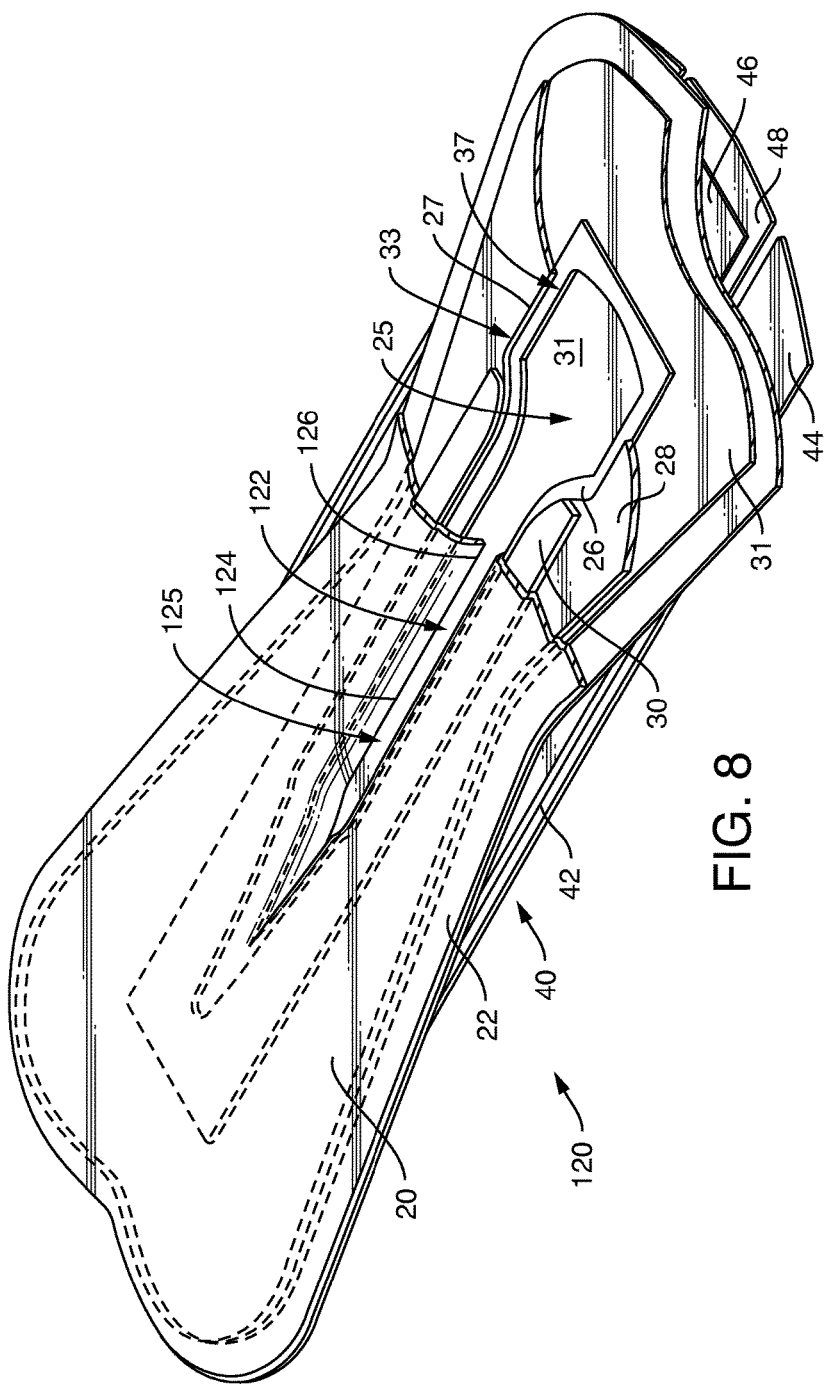
FIG. 8 representatively illustrates a top perspective view of the embodiment of FIG. 7 with portions cut away to illustrate underlying structure.

In some embodiments, the top sheet may have an opening aligned with one or more of the other openings 32, 36, and/or 90. For example, FIGS. 7 and 8 representatively illustrate another exemplary absorbent article 120 having a fourth opening 122. FIG. 7 is a top perspective view of the absorbent article 120. FIG. 8 is a top perspective view of the absorbent article 120 with portions cut away to illustrate underlying structure.

The fourth opening 122 defines a fourth opening peripheral edge 124 and defines a fourth opening area 125. In some embodiments, the fourth opening 122 may have a fourth opening area 125 less than the openings 32, 36, and/or 90 as illustrated in FIG. 8. In these embodiments, the peripheral edge 124 of the fourth opening 122 may be bonded to the lower distribution/intake layer 31 forming an inner peripheral sealed edge 126. Forming an inner peripheral sealed edge 126 may be beneficial for containing superabsorbent polymer or other absorbent materials within the various absorbent layers. In various embodiments, the peripheral edge of the fourth opening may be bonded to the absorbent pledget, the body side absorbent layer, the upper distribution/intake layer, the lower distribution/intake layer, or combinations thereof.

In various embodiments, the liquid permeable top sheet 20 may be made from any suitable material or combination of materials that are adapted to handle menses and/or urine. The topsheet 20 may include a layer constructed of any operative material, and may be a composite material. The top sheet 20 can include a woven fabric, a nonwoven fabric, a polymer film, a film-nonwoven fabric laminate or the like, as well as combinations thereof. An exemplary top sheet material is a 20 gsm spunbond web made of 100% polypropylene fibers. In various embodiments, the top sheet material may be treated with a hydrophilic wetting agent.

The substantially liquid-impermeable back sheet 22 may be made from any suitable material or combination of materials. For example, the back sheet 22 may include a polymeric film, a woven fabric, a nonwoven fabric, or the like, as well as combinations or composites thereof. For example, the back sheet may include a polymer film laminated to a woven or nonwoven fabric. In a particular feature, the polymer film can be composed of polyethylene, polypropylene, polyester or the like, as well as combinations thereof. An exemplary back sheet may include 0.9 mil polyethylene film.

The upper distribution/intake layer 30 may be any suitable material adapted for receiving surges of urine. The upper distribution/intake layer 30 may be a single layer of material or multiple layers of material. Suitable upper distribution/intake layers 30 are taught in U.S. Pat. No. 5,562,650 to Everett et al., the entirety of which is incorporated herein where not contradictory. In some embodiments the upper distribution/intake layer 30 may be a single layer of 128 gsm bonded-carded web with through air bonded hollow polypropylene fibers.

The lower distribution/intake layer 31 may include one or more layers. The lower distribution/intake layer 31 may have the same composition as the upper distribution/intake layer 30 or it may be different. An exemplary material for use as the lower distribution/intake layer 31 includes 128-130 gsm bonded-carded web with through air bonded hollow polypropylene fibers.

The material used for the absorbent pledget layer 26 may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In some embodiments, the absorbent pledget layer 26 is a matrix of cellulosic fluff and superabsorbent hydrogel-forming particles. In addition the absorbent pledget layer may be wrapped by a liquid permeable wrapsheet to maintain the integrity when wet and to inhibit migration of absorbent materials.

The cellulosic fluff may comprise a blend of wood pulp fluff. The superabsorbent material may be present in the absorbent in an amount of from about 0 to about 90 weight percent based on total weight. The absorbent material may have a density within the range of about 0.1 to about 0.45 grams per cubic centimeter. In some embodiments the density is greater than 0.25 g/cc. Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 15 times its weight in liquid, and suitably is capable of absorbing more than about 25 times its weight in liquid. Suitable superabsorbent materials are readily available from various suppliers.

In addition to cellulosic fibers and superabsorbent materials, the absorbent pledget layer may also contain adhesive elements and/or synthetic fibers that provide stabilization and attachment when appropriately activated. Additives such as adhesives may be of the same or different aspect from the cellulosic fibers; for example, such additives may be fibrous, particulate, or in liquid form; adhesives may possess either a curable or a heat-set property. Such additives can enhance the integrity of the bulk absorbent structure, and, alternatively or additionally, may provide adherence between facing layers of the folded structure.

The absorbent pledget 26 may be a single layer of absorbent materials or may be a multilayer structure. Each of the layers can contain similar materials or different materials. Absorbent pledget layer 26 may be partially or wholly wrapped or encompassed by a suitable tissue or nonwoven wrap that aids in maintaining the integrity and shape of the pad. One suitable wrapsheet is 12 gsm wettable spunbond-meltblown-spunbond laminate.

The body side absorbent layer 28 may be a single layer of absorbent material or may be a multiple layer structure. In some embodiments, the body side absorbent layer 28 may be made with the same materials as described above with regard to the absorbent pledget 26. In some embodiments, the body side absorbent layer 28 is a thermally-bonded, stabilized airlaid fibrous web such as 100 gsm airlaid. The body side absorbent layer may optionally include a similar, stabilized airlaid fibrous web. In some embodiments, the absorbent body may include a body side absorbent layer having 30-50% or about 40% superabsorbent material in combination with an absorbent pledget having 50-70% or about 60% superabsorbent material.

The garment attachment adhesive 46 may be applied to the garment side of the back sheet 22. The garment attachment adhesive 46 may be composed of any suitable adhesive. For example, the garment attachment adhesive 46 may be a pressure-sensitive adhesive such as EASYMELT 34-5602, available from National Starch and Chemical Company.

The peel strip 48 may be added to cover the garment attachment adhesive 46 to prevent adhesive contamination. Examples of suitable peel strips 48 include a silicone coated Kraft paper, a silicone coated film, or the like. Other release coatings include coatings containing polytetrafluoroethylene.

The containment flaps 40 of the present invention may consist of a carrier web 44, containment elastics 42, and construction adhesive (not shown). The flap carrier web 44 is desirably constructed of a liquid impermeable material, but may instead be constructed of a liquid permeable material. An example of an acceptable carrier web is a 26.5 gsm spunbond web made of polypropylene fibers. A wide variety of elastic materials may be used for the containment elastics 42. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example, with the application of heat, such that elastic retractive forces are imparted to the substrate.

In some aspects, any of the various absorbent articles with the various openings described herein may be part of one or more arrays of products. For example, referring now to FIG. 9, a first array 130 of products is representatively illustrated. The first array 130 includes a first absorbent article 132 and a second absorbent article 134. Both the first absorbent article 132 and the second absorbent article 134 are illustrated with portions cut away to illustrate underlying features.

The first absorbent article of the first array 130 may have any combination of the features of the absorbent articles described herein. For example, the first absorbent article 132 may include a first body side liner 136, a first back sheet 138, and a first absorbent body 140 positioned between the first body side liner 136 and the first back sheet 138. The first absorbent body 140 includes a first opening 142 and defines a first absorbent body length 144. The first opening 142 defines a first opening length 146 that is at least 50% the first absorbent body length 144. The first opening 142 defines a first opening shape 148. The first opening shape 148 includes an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width.

The second absorbent article of the first array 130 may have any combination of the features of the absorbent articles described herein. For example, the second absorbent article 134 may include a second body side liner 152, a second back sheet 154, and a second absorbent body 156 positioned between the second body side liner 152 and the second back sheet 154. The second absorbent body 156 includes a second opening 158 and defines a second absorbent body length 160. The second opening 158 defines a second opening length 162 that is at least 50% the second absorbent body length 160. The second opening 158 defines a second opening shape 164. The second opening shape 164 includes an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width.

In the first array 130, the first opening shape 148 is the same as or is substantially the same as the second opening shape 164. In various embodiments of the first array 130, the first absorbent body length 144 may be greater than, less than, or the same as the second absorbent body length 160. In some embodiments, the first absorbent body length 144 may be at least 10%, at least 15%, or at least 20% greater than the second absorbent body length 160. In various embodiments of the first array 130, the first opening 142 may define a first opening area and the second opening 164 may define a second opening area wherein the first opening area is greater than, less than, or the same as the second opening area.

Figure 9:
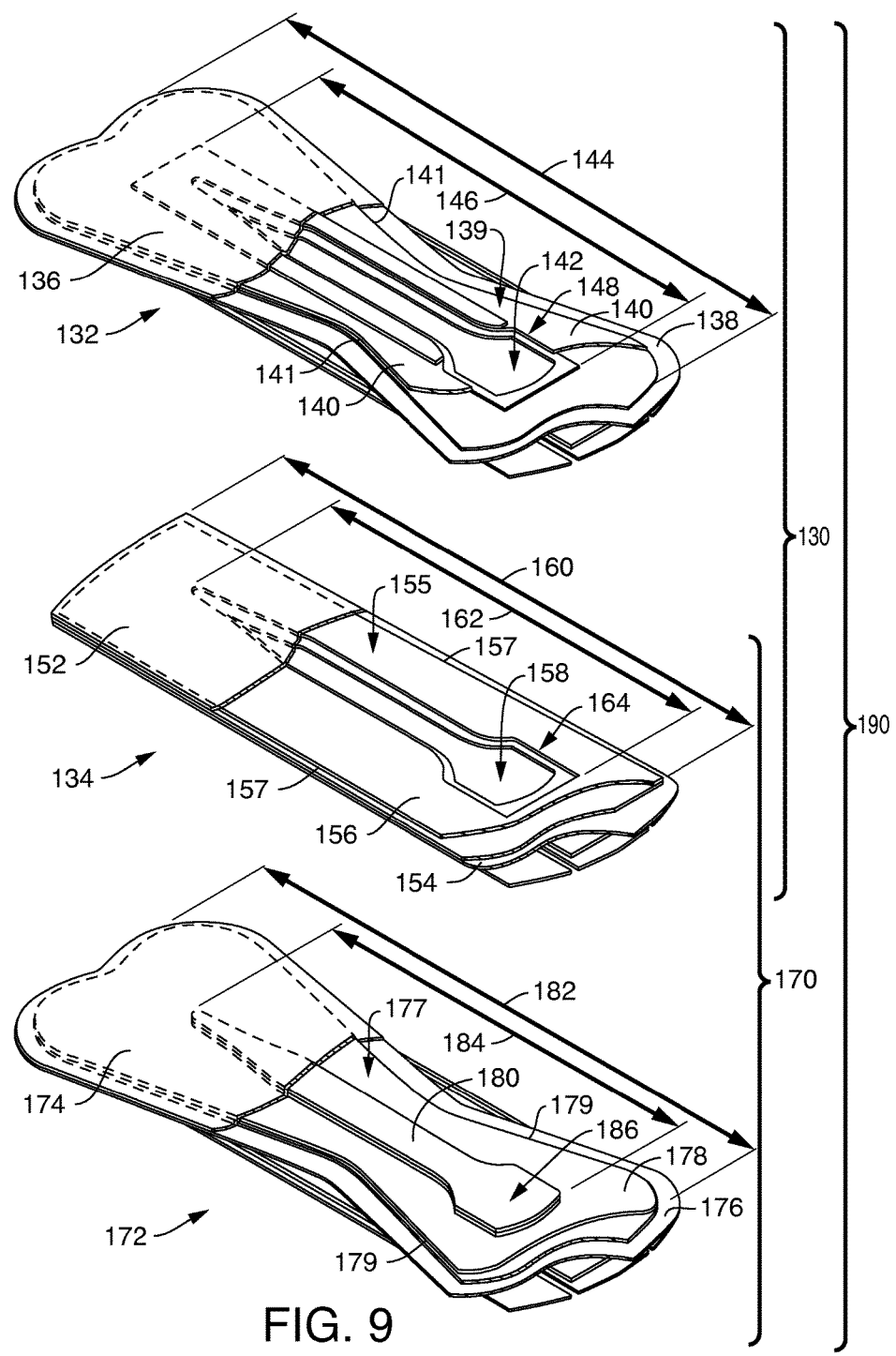
FIG. 9 representatively illustrates exemplary arrays of articles of the present invention.

In various embodiments of the first array 130, the first absorbent body 140 defines a first absorbent body peripheral edge 141 that defines a first absorbent body shape 139. Likewise, the second absorbent body 156 includes a second absorbent body peripheral edge 157 that defines a second absorbent body shape 155. In various embodiments of the first array, the first absorbent body shape may be the same as the second absorbent body shape. In other embodiments of the first array 130, the first absorbent body shape 139 is different than the second absorbent body shape 155. For example, as illustrated in FIG. 9, the first absorbent body shape 139 is curved with concave side edges and rounded ends. In comparison, the second absorbent body shape 155 is generally rectangular.

Referring again to FIG. 9, a second array 170 of products is representatively illustrated. The second array 170 includes the second absorbent article 134 described above and a third absorbent article 172. The third absorbent article 172 is illustrated with portions cut away to illustrate underlying features.

The second absorbent article 134 of the second array 170 may have any combination of the features of the absorbent articles described herein. The third absorbent article 172 of the second array 170 may include any combination of the features of the absorbent articles described herein. For example, the third absorbent article 172 may include a third body side liner 174, a third back sheet 176, and a third absorbent body 178 positioned between the third body side liner 174 and the third back sheet 176. The third absorbent body 178 defines a third absorbent body length 182. The third absorbent article 172 also includes a body conforming structure 180 that defines a body conforming structure length 184 that is at least 50% the third absorbent body length 182. The body conforming structure 180 defines a body conforming structure shape 186. The body conforming structure shape 186 includes an anterior portion having a median anterior portion width, a posterior portion having a median posterior portion width, and a central portion positioned between the anterior portion and the posterior portion and having a median central portion width. The median anterior portion width is greater than the median central portion width and the median central portion width is greater than the median posterior portion width. The body conforming structure 180 is positioned in direct facing relation with the third body side liner 174. The body conforming structure 180 may be positioned between the third body side liner 174 and the third absorbent body 178 as illustrated in FIG. 9. In other embodiments, the body conforming structure may be positioned on the opposite side of the third body side liner (not illustrated). Other suitable body conforming structures are described in the U.S. Patent Application entitled "Absorbent Article With Raised Body Conforming Structure" (Ser. No. 13/412,169) by Dieringer et al. and filed on the same date as the present application. The entirety of said application is incorporated herein by reference in its entirety except where contradictory.

In the second array 170, the second opening shape 164 is the same or is substantially the same as the body conforming structure shape 186. In various embodiments of the second array 170, the second absorbent body length 160 may be greater than, less than, or the same as the third absorbent body length 182. In some embodiments, the second absorbent body length 160 may be at least 10%, at least 15%, or at least 20% greater than the third absorbent body length 182. In some embodiments, the second absorbent body length 160 may be at least 10%, at least 15%, or at least 20% less than the third absorbent body length 182. In various embodiments of the second array 170, the second opening 158 may define a second opening area and the body conforming structure 180 may define a body conforming structure area wherein the second opening area is greater than, less than, or the same as the body conforming structure area.

In various embodiments of the second array 170, the second absorbent body 156 defines a second absorbent body peripheral edge 157 that defines a second absorbent body shape 155. Likewise, the third absorbent body 178 defines a third absorbent body peripheral edge 179 that defines a third absorbent body shape 177. In various embodiments of the second array, the second absorbent body shape may be the same as the third absorbent body shape. In other embodiments of the second array 170, the second absorbent body shape 155 is different than the third absorbent body shape 177. For example, as illustrated in FIG. 9, the second absorbent body shape 155 is generally rectangular. In comparison, the third absorbent body shape 177 is generally curved with concave side edges and rounded ends.

Referring again to FIG. 9, a third array 190 of products is representatively illustrated. The third array 190 includes the first absorbent article 132 described above, the second absorbent article 134 described above, and the third absorbent article 172 described above. However, in various embodiments, the first absorbent article 132, the second absorbent article 134, and/or the third absorbent article 172 of the third array 190 may include any combination of features of the absorbent articles described herein. In the third array 190, the first opening shape 148, the second opening shape 164, and the body conforming structure shape 186 are the same or are substantially the same. In various embodiments of the third array 190, the first absorbent body length 144 may be greater than, less than, or the same as the second absorbent body length 160 and/or the third absorbent body length 182. In various embodiments of the third array 190, the first absorbent body shape 148 may be the same as or different than the second absorbent body shape 155 and/or the third absorbent body shape 177.

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. An array of absorbent articles comprising,
   a first absorbent article comprising
      a first body side liner,
      a first back sheet,
      a first absorbent body positioned between the first body side liner and the first back sheet wherein the first absorbent body includes a first opening and defines a first absorbent body length, the first opening having a first opening length that is at least 50% the first absorbent body length and defining
   a first longitudinal centerline and a first lateral centerline,
   a first opening area,
   a first opening shape,
   an anterior portion having a median anterior portion width,
   a posterior portion having a median posterior portion width, and
   a central portion positioned between the anterior portion and the posterior portion and having a median central portion width, wherein the median anterior portion width is greater than the median central portion width and the median central portion width is greater than the median posterior portion width, wherein the anterior portion of the first opening includes a well having two longitudinal edges, wherein each well longitudinal edge has a section that is generally parallel to the longitudinal centerline, the central portion of the first opening includes a channel having two longitudinal edges, wherein each channel longitudinal edge has a section that is generally parallel to the longitudinal centerline, and the posterior portion of the first opening includes a taper wherein the well transitions into the channel via a first convex transition and a first concave transition and wherein the channel transitions into the taper via a second convex transition, a second absorbent article comprising
- a second body side liner,
- a second back sheet,
- a second absorbent body positioned between the second body side liner and the second back sheet wherein the second absorbent body includes a second opening and defines a second absorbent body length,
- the second opening having a second opening length that is at least 50% the second absorbent body length and defining
- a second opening area,
- a second opening shape,
- an anterior portion having a median anterior portion width,
- a posterior portion having a median posterior portion width, and
- a central portion positioned between the anterior portion and the posterior portion and having a median central portion width, wherein the median anterior portion width is greater than the median central portion width and the median central portion width is greater than the median posterior portion width,
- wherein the anterior portion of the second opening includes a well having two longitudinal edges, wherein each well longitudinal edge has a section that is generally parallel to the longitudinal centerline, the central portion of the second opening includes a channel having two longitudinal edges, wherein each channel longitudinal edge has a section that is generally parallel to the longitudinal centerline, and the posterior portion of the second opening includes a taper wherein the well transitions into the channel via a third convex transition and a second concave transition and wherein the channel transitions into the taper via a fourth convex transition, wherein the first absorbent body length is at least 10% greater than the second absorbent body length and wherein the first opening shape is the same as the second opening shape.

2. The array of claim 1 wherein the first absorbent body includes a first absorbent body peripheral edge that defines a first absorbent body shape and the second absorbent body includes a second absorbent body peripheral edge that defines a second absorbent body shape that is different than the first absorbent body shape.

3. The array of claim 1 further comprising a third absorbent article, the third absorbent article comprising,
- a third body side liner,
- a third back sheet,
- a third absorbent body positioned between the third body side liner and the third back sheet, and
- a body conforming structure positioned in direct facing relation with the third body side liner, wherein the body conforming structure is aligned with a longitudinal centerline of the absorbent article and wherein the body conforming structure defines
- an anterior portion having a median anterior portion width,
- a posterior portion having a median posterior portion width, and
- a central portion positioned between the anterior portion and the posterior portion and having a median central portion width, wherein the median anterior portion width is greater than the median central portion width and the median central portion width is greater than the median posterior portion width, and
- wherein the body conforming structure includes a peripheral edge that defines a body conforming shape that is the same as the first opening shape and the second opening shape.

4. The array of claim 3 wherein the third absorbent body defines a third absorbent body length and the body conforming structure defines a body conforming structure length that is at least 50% the third absorbent body length.

* * * * *